(12) United States Patent
Yoon

(10) Patent No.: US 6,418,935 B1
(45) Date of Patent: Jul. 16, 2002

(54) GLUTEUS MEDIUS MUSCLE PEDICLE BONE GRAFTING FOR TREATMENT OF OSTEONECROSIS OF THE FEMORAL HEAD

(76) Inventor: Taek-Rim Yoon, 104-402 Keumho Apt., #1130 Poongam-Dong, Seo-Gu, Kwangju (KR), 502-156

( * ) Notice: Subject to any disclaimer, the term of this patent is extended or adjusted under 35 U.S.C. 154(b) by 0 days.

(21) Appl. No.: 09/699,526

(22) Filed: Oct. 30, 2000

(51) Int. Cl.[7] ............................................. A61B 19/00
(52) U.S. Cl. ..................................................... 128/898
(58) Field of Search ...................... 128/898; 606/79–86, 606/89

(56) References Cited

PUBLICATIONS

Baksi DP: Treatment of osteonecrosis of the femoral head by drilling and muscle–pedicle bone grafting. J. Bone Joint Surg Mar. 1991; 73–B:241–245.
Baksi DP: Treatment of Post–traumatic avascular necrosis of the femoral head by multiple drilling and muscle–pedicle bone grafting. J. Bone Joint Surg May 1983; 65–B: 268–273.
Bonfiglio, M., et al.: Treatment of bone–grafting of aseptic necrosis of the femeral head and non–union of the femoral neck (Phemister technique) J. Bone Joint Surg., 40–A: 1329–1346, Dec. 1958.
Bonfiglio et al.: Aseptic necrosis of the femoral head and non–union of the femoral neck. Effect of treatment by drilling and bonegrafting)Phemister technique) J. Bone Joint Surg., 50–A: 48–66, Jan. 1968.
Cheung HS et al.: Vascularized iliac crest Grafts: Evaluation of viability status with marrow scintigraphy. Radiology 186:241–245, 1993.
Cho BC et al.: Treatment of osteonecrosis of the femoral head with free vascularized fibular transfer. Ann Plast Surg. 1998 Jun.:40(6):586–93.
Leung PC: Femoral head reconstruction and revascularization. Treatment for ischemic necrosis. Clin Orthop, 323:139–145, 1996.
Malizos KN et al.: Free vascularized fibular graft: a versatile graft for reconstruction of large skeletal defects and revascularization of necrotic bone. Microsurgery. 1992; 13(4):182–7.
Sotereanos DG et al.: Free Vascularized Fibula grafting for the treatment of osteonecrosis of the femoral head. Clin Orthop. 344:243–265. 1997.
Tang CL et al: Donor site morbidity following vascularized fibular grafting. Microsurgery. 1998;18(6):383–6.
Urbaniak JR et al: Treatment of osteonecrosis of the femoral head with free vascularized fibular grafting. J. Bone Joint Surg. 77A:681–694. 1995.
Yoo, MC et al: Free vascularized fibula grafting for the treatment of osteonecrosis of the femoral head; Clinical Orthopaedes and Related Research; No. 272:128–138, Apr. 1992.

*Primary Examiner*—Corrine McDermott
*Assistant Examiner*—Thomas C. Barrett
(74) *Attorney, Agent, or Firm*—Merchant & Gould P.C.

(57) ABSTRACT

A method to treat a disease called osteonecrosis of the femoral head which is caused by interruption of blood supply to the femoral head. This method includes several surgical techniques including detachment of bone block with attachment of a portion of muscle called Gluteus medius from the ilium of pelvis, curettage of dead bone from the femoral head through a window made in the femoral neck and head junction, insertion of the bone block into the femoral head and impaction of the bone chips, and reconstruction of the donor site with bone and/or bone substitutes. The purpose of these procedures is to make the femoral head viable by reestablishing blood supply to the femoral head.

1 Claim, 5 Drawing Sheets

GLUTEUS MEDIUS MUSCLE PEDICLE BONE GRAFTING FOR TREATMENT OF OSTEONECROSIS OF THE FEMORAL HEAD

BACKGROUND OF THE INVENTION

The present invention relates to a surgical method of reestablishing blood supply to the femoral head, which is avascular by a pathologic condition. This method prevents destruction of the femoral head and treats a disease called osteonecrosis of the femoral head, which is caused by interruption of blood supply to the femoral head. This method is composed of several surgical techniques including detachment of a bone block with attachment of a portion of muscle called Gluteus medius from the ilium of pelvis, curettage of dead bone from the femoral head through a window made in the femoral neck and head junction, insertion of the bone block into the femoral head and impaction of the bone chips, and reconstruction of the donor site with bone and/or bone substitutes.

Osteonecrosis of the femoral head is a disease resulting from an interruption of the blood supply to the femoral head. This condition leads to the destruction of the femoral head making the patients feel pain in the hip joint, limitation of joint motion, limping and, if it is severe, inability to walk.

There have been many kinds of surgical methods to treat this disease including core decompression, multiple drilling, osteotomy, bone grafting, and hip replacement. The fact that there have been many methods to treat this disease implies that there has been no single best method. The present invention is a kind of bone grafting. The previous methods of bone grafting can be divided into two categories: non-vascularized bone grafting and vascularized bone grafting.

The present invention is a kind of vascularized bone grafting which is superior to nonvascularized bone grafting. The previous methods of vascularized bone grafting were vascularized fibular grafting, vessel pedicle iliac grafting, and muscle pedicle bone grafting. The present invention is a kind of muscle pedicle bone grafting.

There have been several methods of muscle pedicle bone grafting. The muscles used for this procedure are two kinds: Quadratus femoris and Gluteus medius muscles in which the bone block was detached from the proximal femur and Sartorius and Tensor fascia lata muscle in which the bone block was detached from the ilium. The present invention uses Gluteus medius muscle with attachment of a bone block from the ilium and this point is one feature of this invention.

Even though there have been many methods to treat osteonecrosis of the femoral head, each method has advantages and disadvantages and there has been no single safe method to preserve the femoral head. Therefore, if the femoral head was destroyed despite efforts to preserve the femoral head, there has been no choice but to replace the hip with an artificial joint.

SUMMARY OF THE INVENTION

The present invention is a surgical method of reestablishing blood supply to the femoral head, which is in a avascular status by a pathologic condition by a method of muscle pedicle bone grafting. The invention uses Gluteus medius muscle with attachment of ilium in order to preserve the blood supply to the femoral head via the muscle. The method is composed of several surgical techniques including detachment of a bone block with attachment of a part of muscle called Gluteus medius from the ilium of the pelvis, curettage of dead bone from the femoral head through a window made in the femoral neck and head junction, insertion of the bone block into the femoral head and impaction of the bone chips, and reconstruction of the donor site with bone and/or bone substitutes. This invention has many advantages including: easy technique, strong support of the osteochondral portion of the femoral head which is important to prevent collapse of the femoral head, stable blood supply to the femoral head, early union of the bone graft, early rehabilitation, and minimal donor site discomfort.

BRIEF DESCRIPTION OF THE DRAWINGS

For a better understanding of the nature and objects of the invention, reference should be made to the following detailed description taken in conjunction with the accompanying drawings in which.

DETAILED DESCRIPTION OF THE INVENTION

Figure 1:
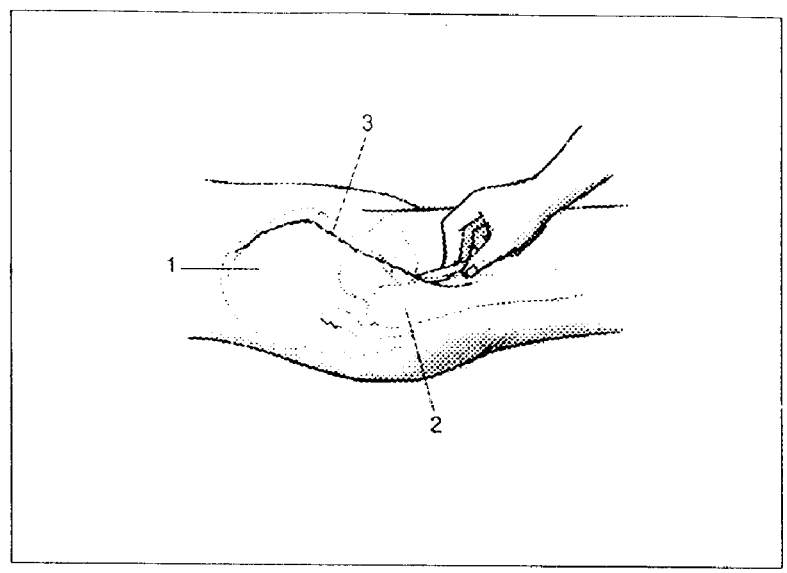
FIG. 1 is a schematic diagram illustrating the patient position and skin incision.
Figure 2:
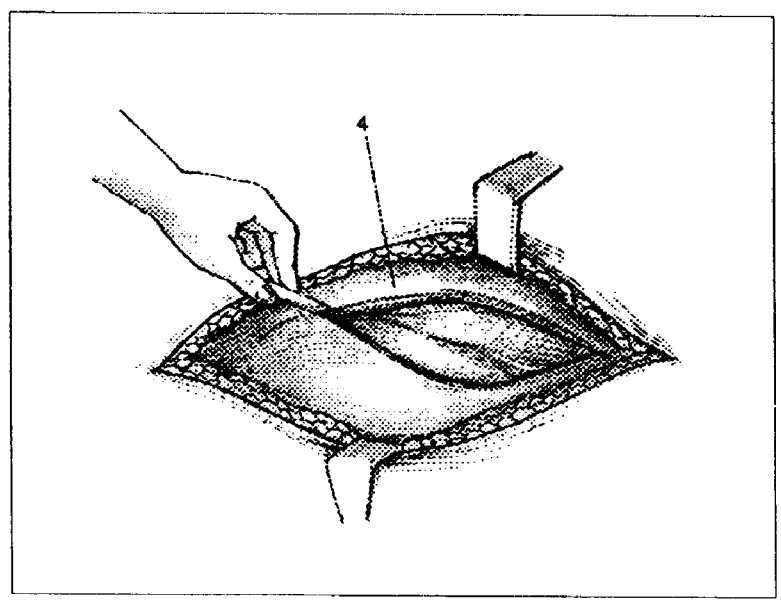
FIG. 2 is a schematic diagram illustrating the incision of fascia and subcutaneous tissue.

A preferred embodiment of the invention will now be described in detail with reference to the accompanying drawings. First of all, with the patient in the semi-lateral decubitus position, a curved incision made 3 is over the ilium 1, hip and the femur 2 as in FIG. 1. The deep fascia 4 and soft tissues are then incised along the line of the skin incision (see FIG. 2).

Figure 3:
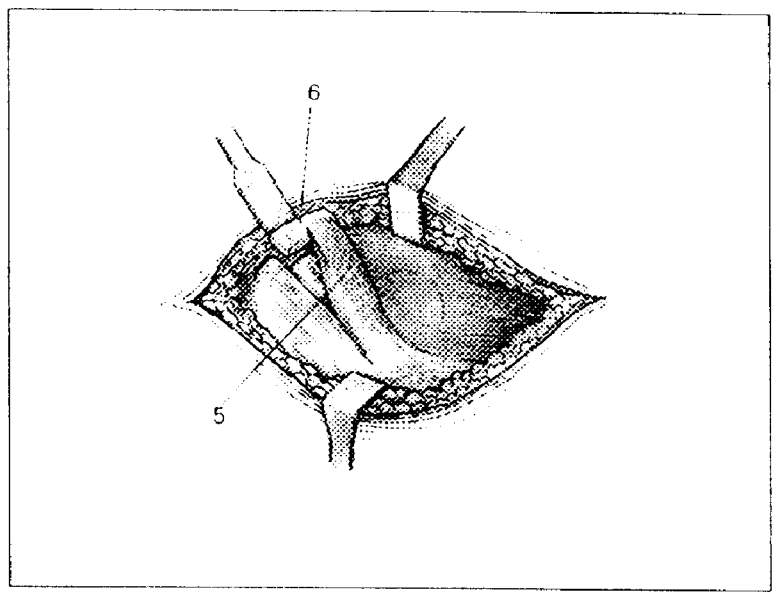
FIG. 3 is a schematic diagram illustrating the detachment of a bone block with attachment of a muscle called gluteus medius from the ilium of pelvis.

The interval between Tensor fascia lata and Gluteus medius muscle is exposed and the small vessels in the interval are ligated. The anterior portion of Gluteus medius 5 is separated from the rest of the muscle for isolation. The iliac crest 6 is exposed and about 4.0 to 5.5 cm by 1.5 to 2.5 cm in depth of iliac crest is marked for removal depending on the patients' size. The inner and outer side of the iliac crest is denuded except for the attachment of an anterior part of Gluteus medius, which is attached to about 2 to 3 cm of an anterior portion of the donor bone block. The bone block is separated from the iliac crest with attachment of anterior portion of Gluteus muscle (see FIG. 3).

The dissection is continued to expose the joint capsule 7. The joint capsule is incised and the femoral head 8 is exposed. The joint capsule is incised longitudinally and the upper and lower margin is incised transversely to expose the femoral head.

Figure 4:
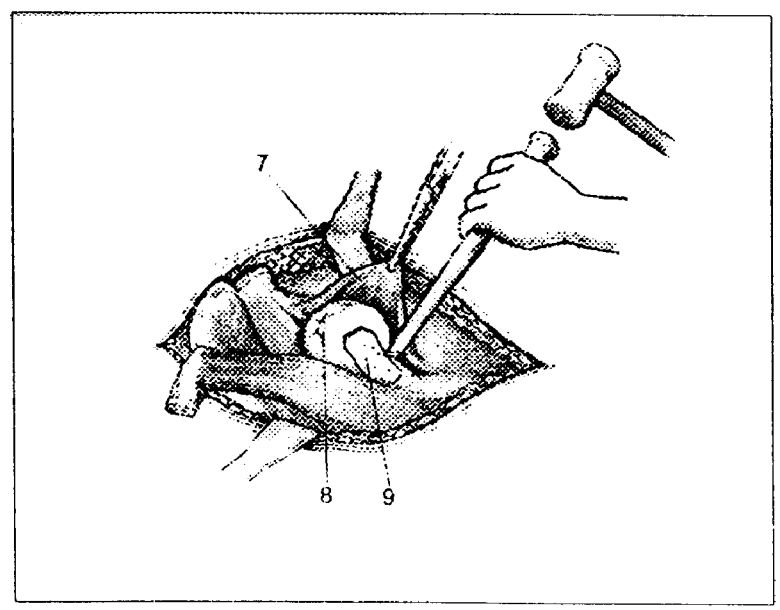
FIG. 4 is a schematic diagram illustrating the procedure making a window in the anterior part of the, femoral head and neck using surgical instruments.
Figure 5:
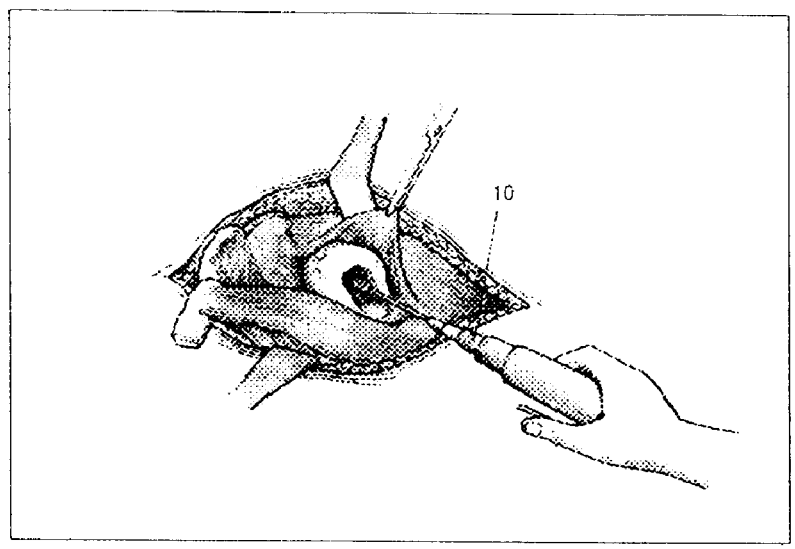
FIG. 5 is a schematic diagram illustrating the curettage of necrotic bone within the femoral head.
Figure 6:
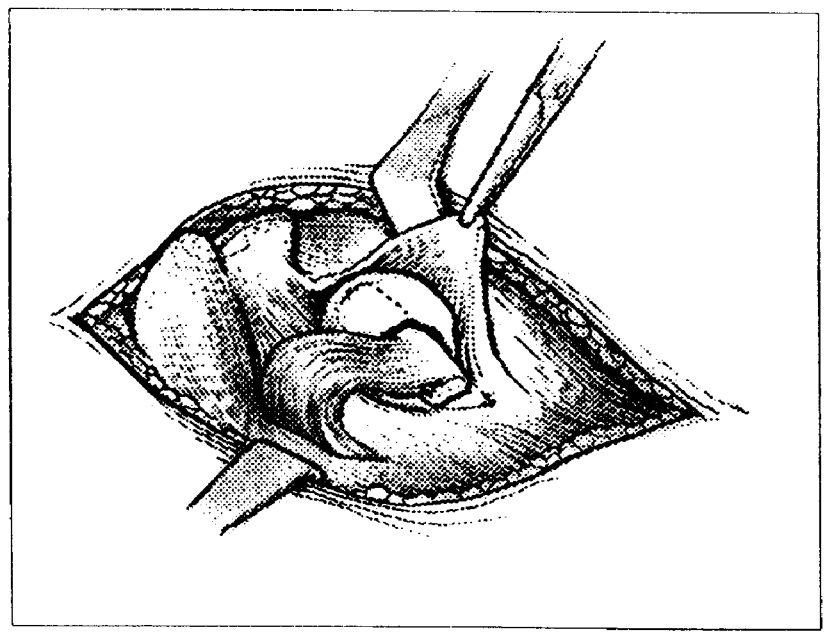
FIG. 6 is a schematic diagram illustrating the insertion of a bone block into the femoral head with a part of muscle attached.
Figure 7:
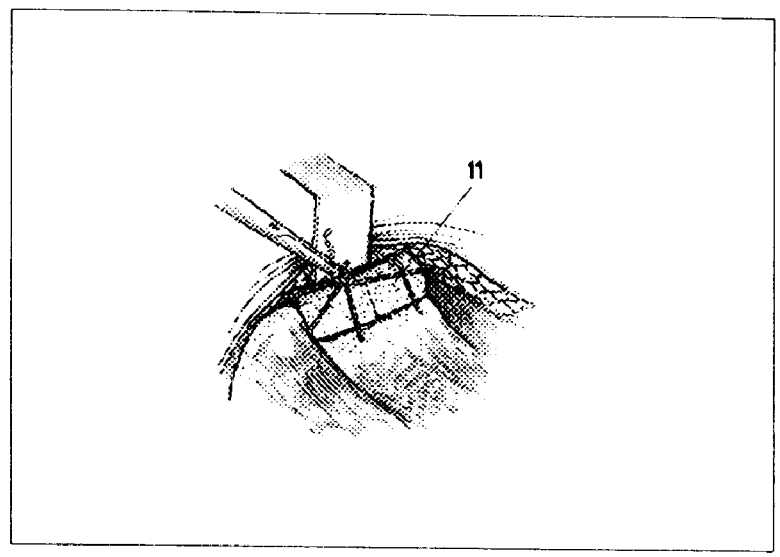
FIG. 7 is a schematic diagram illustrating the reconstruction of the donor site with bone and/or bone substitutes.
Figure 8:
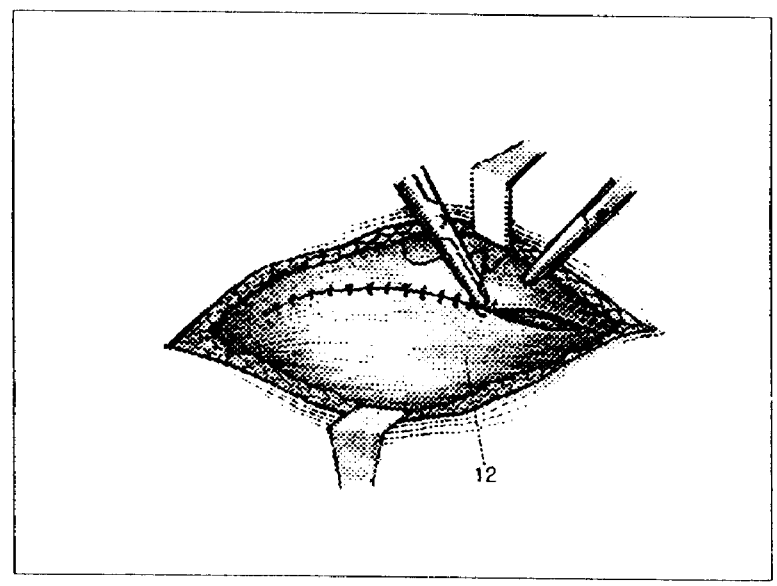
FIG. 8 is a schematic diagram illustrating the suture of the fascia and subcutaneous tissue.
Figure 9:
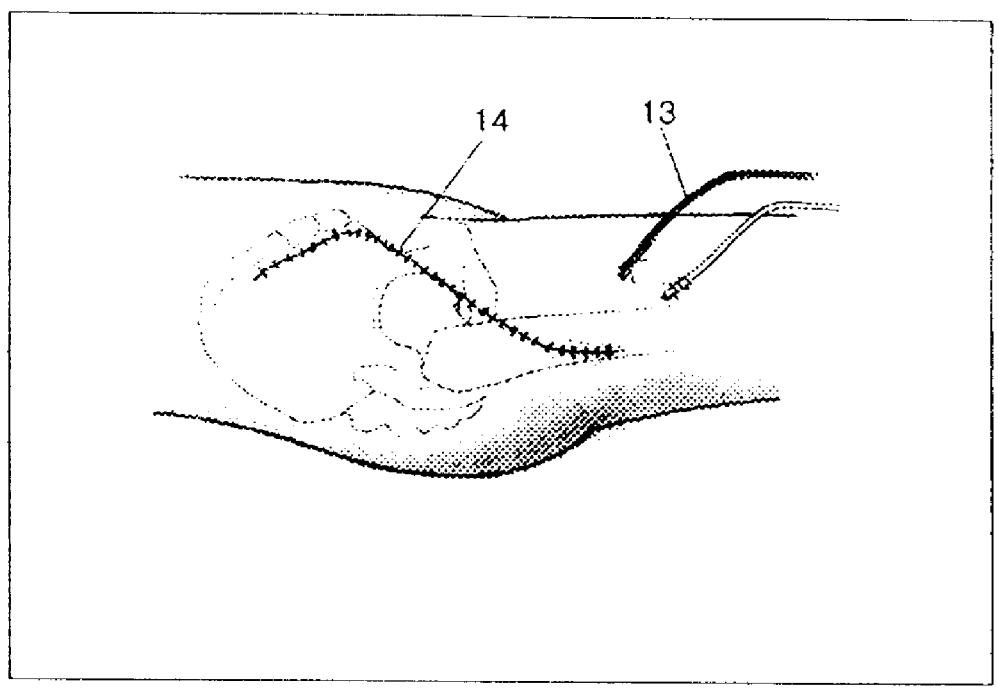
FIG. 9 is a schematic diagram illustrating the skin suture as a final procedure.

A window 9 is made on the anterior neck and head junction (see FIG. 4). The dead bone is removed with a high speed burr 10 or other instruments through the window 9 (see FIG. 5). The viable bone chips are taken out from the femoral head and neck portion with a chisel or gouge for later use. If the femoral head is collapsed, the collapsed portion is elevated with an elevator or other instruments. The window 9 is trimmed for the insertion of the iliac bone block. The size of the bone block should be matched to the window for tight impaction of the bone block. The bone block is then inserted into the femoral head (see FIG. 6), and bone chips are impacted into empty spaces between the cartilage cap and the iliac bone block. The joint capsule is not closed. The donor site of the iliac crest is then reconstructed with the insertion of bone or with bone substitutes 11 (see FIG. 7). They are tied with a suture to the host bone in order not to be dislodged. The muscle fascia 12 and subcutaneous tissue are repaired over a suction drain 13, and the skin is then closed 14.

The patients are recommended to have bed rest for one or two weeks with the affected leg flexed about 30 degrees and abducted about 20 to 30 degrees to relieve the muscular tension. The patients are encouraged to walk without bearing weight after one or two weeks postoperatively and this non-weight bearing is continued until solid union of the bone graft and revascularization of the femoral head.

EFFECT OF THE INVENTION

Osteonecrosis of the femoral head is a disease resulting from an interruption of the blood supply to the femoral head. This condition, if not treated well, leads to the destruction of the femoral head making the patients feel pain in the hip joint, limitation of the joint motion, limping and, if it is severe, inability to walk, and finally leads to complete destruction of the joint and the joint needs to be replaced with an artificial joint.

The invention is a surgical method of revascularizing the femoral head to treat this disease. The invention has many advantages such as: easy technique, strong support of the osteochondral portion of the femoral head which is important to prevent collapse of the femoral head, stable blood supply to the femoral head, early union of the bone graft, early rehabilitation, and minimal donor site discomfort. With this invention, the osteonecrosis of the femoral head can be treated more easily and successfully with minimal discomfort of the patients.

What is claimed is:

1. A surgical method to treat osteonecrosis of the femoral head, the method comprising:

surgically detaching an iliac bone block attached with a portion of Gluteus medius muscle;

surgically removing the necrotic portion of the femoral head through a window made in the femoral head and neck junction;

surgically grafting the iliac bone block attached with a portion of Gluteus medius muscle into the femoral head;

surgically reconstructing the donor site with a bone block or bone substitutes;

detaching the iliac bone block from the donor site with a portion of Gluteus medius muscle;

grafting the portion of the bone block that is not attached with the muscle into the femoral head; and placing the other portion of the bone block that is attached with the muscle on the femoral neck portion in order to preserve vascularity through the muscle into the femoral head.

\* \* \* \* \*